(12) United States Patent
Hallinan et al.

(10) Patent No.: US 8,969,613 B2
(45) Date of Patent: Mar. 3, 2015

(54) REMOVAL OF ALDEHYDES IN ACETIC ACID PRODUCTION

(71) Applicant: Lyondell Chemical Technology, L.P., Houston, TX (US)

(72) Inventors: Noel C. Hallinan, Loveland, OH (US); Brian A. Salisbury, Beach City, TX (US)

(73) Assignee: LyondellBasell Acetyls, LLC, Houston, TX (US)

( * ) Notice: Subject to any disclaimer, the term of this patent is extended or adjusted under 35 U.S.C. 154(b) by 0 days.

(21) Appl. No.: 13/664,549

(22) Filed: Oct. 31, 2012

(65) Prior Publication Data

US 2014/0121404 A1    May 1, 2014

(51) Int. Cl.
  *C07C 47/09* (2006.01)
  *C07C 47/21* (2006.01)
(52) U.S. Cl.
  USPC .......................................... 560/231; 560/233
(58) Field of Classification Search
  CPC ................................ C07C 47/06; C07C 47/21
  USPC ............................ 562/412, 416; 560/231, 233
  See application file for complete search history.

(56) References Cited

U.S. PATENT DOCUMENTS

| | | | |
|---|---|---|---|
| 5,416,237 A | 5/1995 | Aubigne et al. | |
| 5,625,095 A | 4/1997 | Miura et al. | |
| 5,817,869 A | 10/1998 | Hinnenkamp et al. | |
| 5,932,764 A | 8/1999 | Morris et al. | |
| 6,552,221 B1 | 4/2003 | Hallinan et al. | |
| 7,345,197 B1 | 3/2008 | Hallinan et al. | |
| 7,390,919 B1 | 6/2008 | Salisbury et al. | |
| 7,485,749 B2 | 2/2009 | Sawyer et al. | |
| 7,524,988 B2 * | 4/2009 | Harris et al. | 562/608 |
| 8,076,512 B2 | 12/2011 | Fitzpatrick et al. | |
| 2005/0197509 A1 | 9/2005 | Picard et al. | |
| 2009/0209786 A1 | 8/2009 | Scates et al. | |
| 2011/0054213 A1 | 3/2011 | Fitzpatrick et al. | |
| 2011/0251422 A1 * | 10/2011 | Salisbury | 560/238 |

OTHER PUBLICATIONS

PCT International Search Report and Written Opinion mailed Jan. 23, 2014 for PCT/US2013/067266.

* cited by examiner

*Primary Examiner* — Kamal Saeed
*Assistant Examiner* — Janet L. Coppins

(57) ABSTRACT

A system and method for removing acetaldehyde from an acetic acid system, including providing a solution from the acetic acid system, the stream having methyl iodide and acetaldehyde, and contacting the solution with an ion-exchange resin and/or liquid catalyst.

15 Claims, 5 Drawing Sheets

REMOVAL OF ALDEHYDES IN ACETIC ACID PRODUCTION

CROSS-REFERENCE TO RELATED APPLICATIONS

Not applicable.

STATEMENT REGARDING FEDERALLY SPONSORED RESEARCH OR DEVELOPMENT

Not applicable.

FIELD OF THE INVENTION

The disclosure relates to the production of acetic acid. More particularly, the disclosure relates to removal of aldehydes in acetic acid production.

BACKGROUND

This section of this document introduces information about and/or from the art that may provide context for or be related to the subject matter described herein and/or claimed below. It provides background information to facilitate a better understanding of the various aspects of the present invention. This is a discussion of "related" art. That such art is related in no way implies that it is also "prior" art. The related art may or may not be prior art. The discussion in this section of this document is to be read in this light, and not as admissions of prior art.

Production of acetic acid by methanol carbonylation is known. In the current acetic acid production process, a reaction mixture is withdrawn from a reactor and is separated in a flash tank into a liquid fraction and a vapor fraction having acetic acid generated during the carbonylation reaction. The liquid fraction may be recycled to the carbonylation reactor, and the vapor fraction is passed to a separations unit, which by way of example may be a light-ends distillation column. The light-ends distillation column separates a crude acetic acid product from other components. The crude acetic acid product is passed to a drying column to remove water and then is subjected to further separations to recover acetic acid.

One challenge facing the industry is the presence of aldehyde(s) in acetic acid production, which can be present in the feed and also form as an undesired by-product of carbonylation reactions. Processes for removing aldehydes exist; however, there continues to be a need to improve upon, and provide alternatives to, current aldehyde removal processes.

SUMMARY

An aspect of the invention relates to a method for removing acetaldehyde from an acetic acid system, including: providing a solution from the acetic acid system, the stream having methyl iodide and acetaldehyde; and contacting the solution with an ion-exchange resin.

Another aspect of the invention relates to a method of operating an acetic acid production system, including: flashing a reaction mixture discharged from an acetic acid production reactor into a vapor stream and a liquid stream, the vapor stream having acetic acid, water, methanol, methyl acetate, methyl iodide, and acetaldehyde; distilling the vapor stream into a product stream of acetic acid and water, a bottoms stream, and an overhead stream having methyl iodide, water, methyl acetate, acetic acid, and acetaldehyde; condensing the overhead stream into a light, aqueous phase having water, acetic acid, and methyl acetate, and a heavy, organic phase having methyl iodide, acetic acid, water, and the acetaldehyde; and converting the acetaldehyde in at least a portion of the heavy, organic phase to an oligomer.

Yet another aspect relates to a method of producing acetic acid, including: reacting methanol and carbon monoxide in the presence of a carbonylation catalyst to produce a crude stream comprising acetic acid; purifying the crude stream to produce a product stream comprising the acetic acid, wherein the purifying generates a methyl iodide stream comprising methyl iodide acetaldehyde; and contacting the methyl iodide stream with an ion-exchange resin to convert the acetaldehyde to crotonaldehyde to reduce an amount of acetaldehyde in an acetic acid system producing the acetic acid.

Yet another aspect of the invention relates to an acetic acid production system, having: a reactor to react methanol and carbon monoxide in the presence of a carbonylation catalyst to form acetic acid; a flash vessel that receives a reaction mixture comprising the acetic acid from the reactor; a distillation column that receives a vapor stream from the flash vessel; a decanter that receives a condensed overhead stream from the distillation column; and a resin vessel that receives a heavy, organic phase comprising methyl iodide and acetaldehyde from the decanter, the resin vessel having an ion-exchange resin to convert the acetaldehyde to an oligomer.

The above paragraphs present a simplified summary of the presently disclosed subject matter in order to provide a basic understanding of some aspects thereof. The summary is not an exhaustive overview, nor is it intended to identify key or critical elements to delineate the scope of the subject matter claimed below. Its sole purpose is to present some concepts in a simplified form as a prelude to the more detailed description set forth below.

BRIEF DESCRIPTION OF THE DRAWINGS

The claimed subject matter may be understood by reference to the following description taken in conjunction with the accompanying drawings, in which like reference numerals identify like elements, and in which:

While the invention is susceptible to various modifications and alternative forms, the drawings illustrate specific embodiments herein described in detail by way of example. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAIL DESCRIPTION

A detailed description of embodiments of the disclosed process follows. However, it is to be understood that the described embodiments are merely exemplary of the process and that the process may be embodied in various and alternative forms of the described embodiments. Therefore, specific procedural, structural and functional details which are addressed in the embodiments described herein are not to be interpreted as limiting, but merely as a basis for the claims and as a representative basis for teaching one skilled in the art to variously employ the disclosed process.

The designation of groups of the Periodic Table of the Elements as used herein is in accordance with the current IUPAC convention. The expressions "OAc" or "AcO" are used herein as abbreviations for the acetate anion, i.e., $H_3CC(=O)O^-$. The expression "acac" is used herein as an abbreviation for acetoacetate anion, i.e., $H_3CC(=O)CH_2C(=O)O^-$. Unless specifically indicated otherwise, the expression "wt %" as used herein refers to the percentage by weight of a particular component in the referenced composition. With respect to all ranges disclosed herein, such ranges are intended to include any combination of the mentioned upper and lower limits even if the particular combination is not specifically listed.

Embodiments of the disclosed process and system involve the production of acetic acid by carbonylating methanol in a carbonylation reaction. The carbonylation reaction may be represented by:

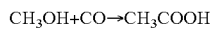

$$CH_3OH + CO \rightarrow CH_3COOH$$

Figure 1:
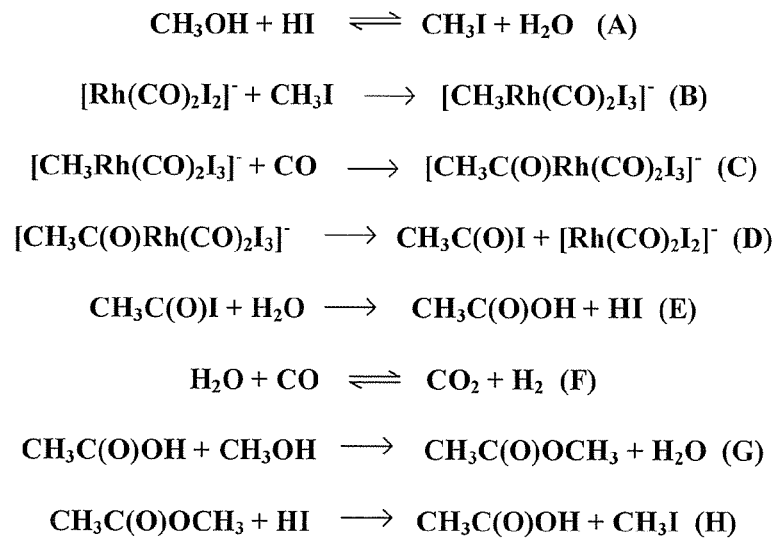
FIG. 1 sets forth some of the interrelated reactions and equilibria believed to be involved in the carbonylation of methanol in the presence of a rhodium catalyst in accordance with embodiments of the present techniques.

The underlying chemistry involves a multiplicity of interrelated reactions, by-products, and equilibria. FIG. 1 sets forth some of the interrelated reactions and equilibria believed to be involved in the carbonylation reaction. As can be seen in FIG. 1, hydrogen iodide ("HI") may be a component in the underlying chemistry for the production of acetic acid.

Embodiments of the disclosed process generally include: (a) obtaining HI in an acetic acid production system; and (b) continuously introducing a complexing agent into the system, wherein the complexing agent and HI interact to form a complex. The following description elaborates upon the disclosed process.

Figure 2:
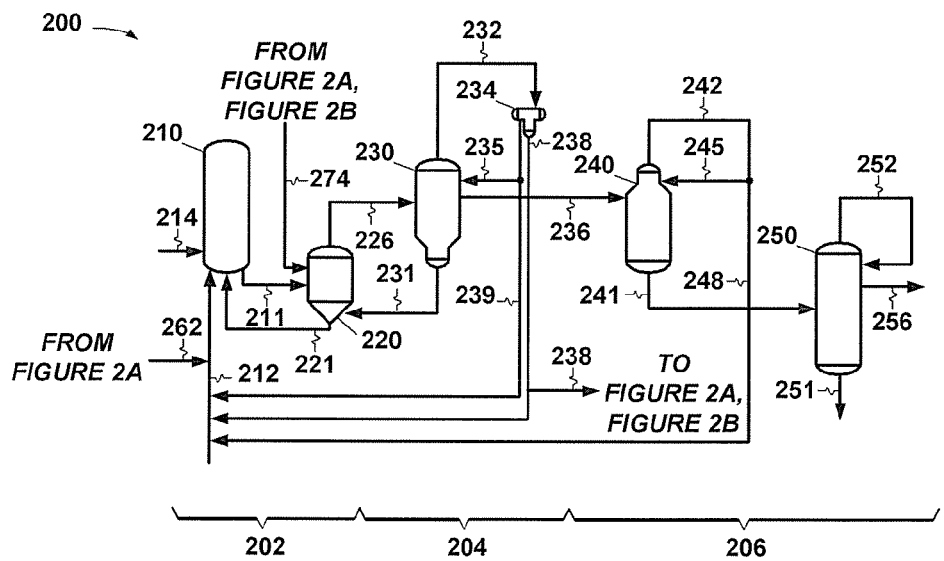
FIG. 2 is a schematic of an exemplary acetic acid production system in accordance with embodiments of the present techniques.

FIG. 2 is a schematic of an exemplary acetic acid production system 200 implementing the carbonylation reaction. In certain embodiments, the acetic acid system 200 may include a reaction area 202, a light-ends area 204, and a purification area 206. The reaction area 202 may include a reactor 210, a flash vessel 220, and associated equipment. The reactor 210 is a reactor or vessel in which methanol is carbonylated in the presence of a catalyst to form acetic acid at elevated pressure and temperature.

The flash vessel 220 is a tank or vessel in which a reaction mixture obtained in the reactor is at least partially depressurized and/or cooled to form a vapor stream and a liquid stream. The liquid stream 221 may be a product or composition which has components in the liquid state under the conditions of the processing step in which the stream is formed. The vapor stream 226 may be a product or composition which has components in the gaseous state under the conditions of the processing step in which the stream is formed.

The light-ends area 204 may include a separations column, for example a light-ends column 230, and associated equipment such as decanter 234. The light-ends column is a fractioning or distillation column and includes equipment associated with the column, such as heat exchangers, decanters, pumps, compressors, valves, and the like. The purification area 206 may include a drying column 240, optionally a heavy-ends column 250, and associated equipment, and so on. The heavy-ends column is a fractioning or distillation column and includes any equipment associated with the column, such as heat exchangers, decanters, pumps, compressors, valves, and the like. Further, as discussed below, various recycle streams may include streams 221, 238, 239, 248. The recycle streams may be products or compositions recovered from a processing step downstream of the flash vessel 220 and which is recycled to the reactor 210, flash vessel 220, or light-ends column 230, and so forth.

In an embodiment, the reactor 210 may be configured to receive a carbon monoxide feed stream 214 and a methanol feed stream 212. A reaction mixture may be withdrawn from the reactor in stream 211. Other streams may be included as known in the art, for example, a stream that may recycle a bottoms mixture of the reactor 210 back into the reactor 210, or a stream may be included to release a gas from the reactor 210.

In an embodiment, the flash vessel 220 may be configured to receive stream 211 from the reactor 210. In the flash vessel 220, stream 211 may be separated into a vapor stream 226 and a liquid stream 221. The vapor stream 226 may be communicated to the light-ends column 230, and the liquid stream 221 may be communicated to the reactor 210. In an embodiment, stream 226 may have acetic acid, water, methyl iodide, methyl acetate, HI, mixtures thereof and the like.

In an embodiment, the light-ends column 230 may be a distillation column and associated equipment such as a decanter 234, pumps, compressors, valves, and other related equipment. The light-ends column 230 may be configured to receive stream 226 from the flash vessel 220. In the illustrated embodiment, stream 232 is the overhead product from the light-ends column 230, and stream 231 is bottoms product from the light-ends column 230. As indicated, light-ends column 230 may include a decanter 234, and stream 232 may pass into decanter 234.

Stream 235 may emit from decanter 234 and recycle back to the light-ends column 230. Stream 238 may emit from decanter 234 and may recycle back to the reactor 210 via, for example, stream 212 or be combined with any of the other streams that feed the reactor. Stream 239 may recycle a portion of the light phase of decanter 234 back to the reactor 210 via, for example, stream 212. Stream 236 may emit from the light-ends column 230. Other streams may be included as known in the art, for example, a stream that may recycle a bottoms mixture of the light-ends column 230 back into the light-ends column 230. Streams received by or emitted from the light-ends column 230 may pass through a pump, compressor, heat exchanger, and the like as is common in the art.

In an embodiment, the drying column 240 may be a vessel and associated equipment such as heat exchangers, decanters, pumps, compressors, valves, and the like. The drying column 240 may be configured to receive stream 236 from the light-ends column 230. The drying column 240 may separate components of stream 236 into streams 242 and 241. Stream 242 may emit from the drying column 240, recycle back to the drying column via stream 245, and/or recycle back to the reactor 210 through stream 248 (via, for example, stream 212). Stream 241 may emit from the drying column 240 and may include de-watered crude acetic acid product. Stream 242 may pass through equipment known in the art, for example, a heat exchanger or separation vessel before streams 245 or 248 recycle components of stream 242. Other streams may be included as known in the art, for example, a stream may recycle a bottoms mixture of the drying column 240 back into the drying column 240. Streams received by or emitted from the drying column 240 may pass through a pump, compressor, heat exchanger, separation vessel, and the like as is common in the art.

The heavy-ends column 250 may be a distillation column and associated equipment such as heat exchangers, decanters, pumps, compressors, valves, and the like. The heavy-ends column 250 may be configured to receive stream 241 from the drying column 240. The heavy-ends column 250 may separate components from stream 241 into streams 251, 252, and 256. Streams 251 and 252 may be sent to additional processing equipment (not shown) for further processing. Stream 252 may also be recycled, for example, to light-ends column 240. Stream 256 may have acetic acid product.

A single column (not depicted) may be used in the place of the combination of the light-ends distillation column 230 and the drying column 240. The single column may vary in the diameter/height ratio and the number of stages according to the composition of vapor stream from the flash separation and the requisite product quality. For instance, U.S. Pat. No. 5,416,237, the teachings of which are incorporated herein by reference, discloses a single column distillation. Alternative embodiments for the acetic acid production system 200 may also be found in U.S. Pat. Nos. 6,552,221, 7,524,988, and 8,076,512, which are herein incorporated by reference.

In an embodiment, the carbonylation reaction in reactor 210 of system 200 may be performed in the presence of a catalyst. Catalysts may include, for example, rhodium catalysts and iridium catalysts.

Suitable rhodium catalysts are taught, for example, by U.S. Pat. No. 5,817,869, which is herein incorporated by reference. The rhodium catalysts may include rhodium metal and rhodium compounds. In an embodiment, the rhodium compounds may be selected from the group consisting of rhodium salts, rhodium oxides, rhodium acetates, organo-rhodium compounds, coordination compounds of rhodium, the like, and mixtures thereof. In an embodiment, the rhodium compounds may be selected from the group consisting of Rh2(CO)4I2, Rh2(CO)4Br2, Rh2(CO)4Cl2, Rh(CH3CO2)2, Rh(CH3CO2)3, [H]Rh(CO)2I2, the like, and mixtures thereof. In an embodiment, the rhodium compounds may be selected from the group consisting of [H]Rh(CO)2I2, Rh(CH3CO2)2, the like, and mixtures thereof.

Suitable iridium catalysts are taught, for example, by U.S. Pat. No. 5,932,764. The iridium catalysts may include iridium metal and iridium compounds. Examples of suitable iridium compounds include IrCl3, IrI3, IrBr3, [Ir(CO)2I]2, [Ir(CO)2Cl]2, [Ir(CO)2Br]2, [Ir(CO)4I2]-H+, [Ir(CO)2Br2]-H+, [IR(CO)2I2]-H+, [Ir(CH3)I3(CO)2]-H+, Ir4(CO)12, IrCl3.4H2O, IrBr3.4H2O, Ir3(CO)12, Ir2O3, IrO2, Ir(acac)(CO)2, Ir(acac)3, Ir(OAc)3, [Ir3O(OAc)6(H2O)3][OAc], H2[IrCl6], the like, and mixtures thereof. In an embodiment, the iridium compounds may be selected from the group consisting of acetates, oxalates, acetoacetates, the like, and mixtures thereof. In an embodiment, the iridium compounds may be one or more acetates.

In an embodiment, the catalyst may be used with a co-catalyst. In an embodiment, co-catalysts may include metals and metal compounds selected from the group consisting of osmium, rhenium, ruthenium, cadmium, mercury, zinc, gallium, indium, and tungsten, their compounds, the like, and mixtures thereof. In an embodiment, co-catalysts may be selected from the group consisting of ruthenium compounds and osmium compounds. In an embodiment, co-catalysts may be one or more ruthenium compounds. In an embodiment, the co-catalysts may be one or more acetates.

The reaction rate depends upon the concentration of the catalyst in the reaction mixture in reactor 210. In an embodiment, the catalyst concentration may be in a range from about 1.0 mmol to about 100 mmol catalyst per liter (mmol/l) of reaction mixture. In some embodiments the catalyst concentration is at least 2.0 mmol/l, or at least 5.0 mmol/l, or at least 7.5 mmol/l. In some embodiments the catalyst concentration is at most 75 mmol/l, or at most 50 mmol/l, or at least 25 mmol/l. In particular embodiments, the catalyst concentration is from about 2.0 to about 75 mmol/l, or from about 5.0 to about 50 mmol/l, or from about 7.5 to about 25 mmol/l.

In an embodiment, the carbonylation reaction in reactor 210 of system 200 may be performed in the presence of a catalyst stabilizer. Suitable catalyst stabilizers include those known to the industry. In general, there are two types of catalyst stabilizers. The first type of catalyst stabilizer may be a metal iodide salt such as lithium iodide. The second type of catalyst stabilizer may be a non-salt stabilizer. In an embodiment, non-salt stabilizers may be pentavalent Group VA oxides, such as that disclosed in U.S. Pat. No. 5,817,869 which is herein incorporated by reference. In an embodiment, the catalyst stabilizer may be a phosphine oxide. In an embodiment, the catalyst stabilizer may be a triphenylphosphine oxide ("TPPO").

The amount of pentavalent Group VA oxide, when used, generally is such that a ratio to rhodium is greater than about 60:1. Preferably, the ratio of the pentavalent Group 15 oxide to rhodium is from about 60:1 to about 500:1. In some embodiments, from about 0.1 to about 3 M of the pentavalent Group 15 oxide may be in the reaction mixture. More preferably, from about 0.15 to about 1.5 M, or from 0.25 to 1.2 M, of the pentavalent Group 15 oxide may be in the reaction mixture.

In other embodiments, the reaction may occur in the absence of a stabilizer selected from the group of metal iodide salts and non-metal stabilizers such as pentavalent Group 15 oxides. In further embodiments, the catalyst stabilizer may consist of an complexing agent which is brought into contact with the reaction mixture stream 211 in the flash vessel 220.

In an embodiment, hydrogen may also be fed into the reactor 210. Addition of hydrogen can enhance the carbonylation efficiency. In an embodiment, the concentration of hydrogen may be in a range of from about 0.1 mol % to about 5 mol % of carbon monoxide in the reactor 210. In an embodiment, the concentration of hydrogen may be in a range of from about 0.3 mol % to about 3 mol % of carbon monoxide in the reactor 210.

In an embodiment, the carbonylation reaction in reactor 210 of system 200 may be performed in the presence of water. In an embodiment, the concentration of water is from about 2 wt % to about 14 wt % based on the total weight of the reaction mixture. In an embodiment, the water concentration is from about 2 wt % to about 10 wt %. In an embodiment, the water concentration is from about 4 wt % to about 8 wt %.

In an embodiment, the carbonylation reaction may be performed in the presence of methyl acetate. Methyl acetate may be formed in situ. In embodiments, methyl acetate may be added as a starting material to the reaction mixture. In an embodiment, the concentration of methyl acetate may be from about 2 wt % to about 20 wt % based on the total weight of the reaction mixture. In an embodiment, the concentration of methyl acetate may be from about 2 wt % to about 16 wt %. In an embodiment, the concentration of methyl acetate may be from about 2 wt % to about 8 wt %. Alternatively, methyl acetate or a mixture of methyl acetate and methanol from byproduct streams of the methanolysis of polyvinyl acetate or ethylene-vinyl acetate copolymers can be used for the carbonylation reaction.

In an embodiment, the carbonylation reaction may be performed in the presence of methyl iodide. Methyl iodide may be a catalyst promoter. In an embodiment, the concentration of MeI may be from about 0.6 wt % to about 36 wt % based on the total weight of the reaction mixture. In an embodiment, the concentration of MeI may be from about 4 wt % to about 24 wt %. In an embodiment, the concentration of MeI may be from about 6 wt % to about 20 wt %. Alternatively, MeI may be generated in the reactor 210 by adding HI.

In an embodiment, methanol and carbon monoxide may be fed to the reactor 210 in stream 212 and stream 214, respectively. The methanol feed stream to the reactor 210 may come from a syngas-methanol facility or any other source. As seen in FIG. 1, methanol does not react directly with carbon monoxide to form acetic acid. It is converted to MeI by the HI present in the reactor 210 and then reacts with carbon monoxide and water to give acetic acid and regenerate the HI.

In an embodiment, the carbonylation reaction in reactor 210 of system 200 may occur at a temperature within the range of about 120° C. to about 250° C., alternatively, about 150° C. to about 250° C., alternatively, about 150° C. to about 200° C. In an embodiment, the carbonylation reaction in reactor 210 of system 200 may be performed under a pressure within the range of about 200 psig (14 kg/cm$^2$) to 2000 psig (140 kg/cm$^2$), alternatively, about 200 psia (14 kg/cm$^2$) to about 1,000 psia (70 kg/cm$^2$), alternatively, about 300 psia (21 kg/cm$^2$) to about 500 psia (35 kg/cm$^2$).

In an embodiment, the reaction mixture may be withdrawn from the reactor 210 through stream 211 and is flashed in flash vessel 220 to form a vapor stream 226 and a liquid stream 221. The reaction mixture in stream 211 may include acetic acid, methanol, methyl acetate, methyl iodide, carbon monoxide, carbon dioxide, water, HI, heavy impurities, catalyst, or combinations thereof. The flash vessel 220 may generally comprise any configuration for separating vapor and liquid components via a reduction in pressure. For example, the flash vessel 220 may comprise a flash tank, nozzle, valve, or combinations thereof.

The flash vessel 220 may have a pressure below that of the reactor 210. In an embodiment, the flash vessel 220 may have a pressure of from about 10 psig to 100 psig. In an embodiment, the flash vessel 220 may have a temperature of from about 100° C. to 160° C.

The vapor stream 226 may include acetic acid and other volatile components such as methanol, methyl acetate, methyl iodide, carbon monoxide, carbon dioxide, water, entrained HI, complexed HI, and mixtures thereof. The liquid stream 221 may include the catalyst, complexed HI, HI, an azeotrope of HI and water, and mixtures thereof. The liquid stream 221 may further comprise sufficient amounts of water and acetic acid to carry and stabilize the catalyst, non-volatile catalyst stabilizers, or combinations thereof. The liquid stream 221 may recycle to the reactor 210. The vapor stream 226 may be communicated to light-ends column 230 for distillation.

In an embodiment, the vapor stream 226 may be distilled in a light-ends column 230 to form an overhead stream 232, a crude acetic acid product stream 236, and a bottom stream 231. In an embodiment, the light-ends column 230 may have at least 10 theoretical stages or 16 actual stages. In an alternative embodiment, the light-ends column 230 may have at least 14 theoretical stages. In an alternative embodiment, the light-ends column 230 may have at least 18 theoretical stages. In embodiments, one actual stage may equal approximately 0.6 theoretical stages. Actual stages can be trays or packing. The reaction mixture may be fed via stream 226 to the light-ends column 230 at the bottom or the first stage of the column 230.

Stream 232 may include HAc, water, carbon monoxide, carbon dioxide, methyl iodide, methyl acetate, methanol and acetic acid, and mixtures thereof. Stream 231 may have acetic acid, methyl iodide, methyl acetate, HI, water, and mixtures thereof. Stream 236 may have acetic acid, HI, water, heavy impurities, and mixtures thereof.

In an embodiment, the light-ends column 230 may be operated at an overhead pressure within the range of 20 psia (1.4 kg/cm2) to 40 psia (2.8 kg/cm2), alternatively, the overhead pressure may be within the range of 30 psia (2 kg/cm2) to 35 psia (2.5 kg/cm2). In an embodiment, the overhead temperature may be within the range of 95° C. to 135° C., alternatively, the overhead temperature may be within the range of 110° C. to 135° C., alternatively, the overhead temperature may be within the range of 125° C. to 135° C. In an embodiment, the light-ends column 230 may be operated at a bottom pressure within the range of 25 psia (1.8 kg/cm2) to 45 psia (3.2 kg/cm2), alternatively, the bottom pressure may be within the range of 30 psia (2.1 kg/cm2) to 40 psia (2.8 kg/cm2).

In an embodiment, the bottom temperature may be within the range of 115° C. to 155° C., alternatively, the bottom temperature is within the range of 125° C. to 135° C. In an embodiment, crude acetic acid in stream 236 may be emitted from the light-ends column 240 as a liquid sidedraw. Stream 236 may be operated at a pressure within the range of 25 psia (1.8 kg/cm2) to 45 psia (3.2 kg/cm2), alternatively, the pressure may be within the range of 30 psia (2.1 kg/cm2) to 40 psia (2.8 kg/cm2). In an embodiment, the temperature of stream 236 may be within the range of 110° C. to 140° C., alternatively, the temperature may be within the range of 125° C. to 135° C. Stream 236 may be taken between the fifth to the eighth actual stage of the light-ends column 230.

In one or more embodiments, the crude acetic acid in stream 236 may be optionally subjected to further purification, e.g., drying-distillation, in drying column 240 to remove water and heavy-ends distillation in stream 24. Stream 241 may be communicated to heavy-ends column 250 where heavy impurities such as propionic acid may be removed in stream 251 and final acetic acid product may be recovered in stream 256.

The overhead stream 232 from the light-ends column 230 may be condensed and separated in a decanter 234 to form a light, aqueous phase and a heavy, organic phase. A portion or all of the heavy, organic phase may be sent as stream 238 for further processing, as discussed below. Further, a portion of stream 238 may be optionally recycled to the reactor 210 via stream 212, for example. It should be noted that the portion of stream 238 sent for further processing (FIG. 2A or FIG. 2B) and the other portion of the stream 238 recycled to the reactor 210 may each originate as independent streams from the decanter 234 heavy phase. The light aqueous phase from the decanter 234 may be recycled to the light-ends column 230 in stream 235 or may be recycled to the reactor 210 in stream 239 via stream 212, for example.

The heavy, organic phase stream 238 may have HAc, MeI, methyl acetate, hydrocarbons, acetic acid, water, and mixtures thereof. In an embodiment, stream 238 may be essentially non-aqueous with a water concentration of less than 1 wt %. In an embodiment, stream 238 may have MeI greater than 50% by weight of the stream. The light, aqueous phase in streams 236 and 239 may have water (greater than 50% by weight of the stream), acetic acid, methyl acetate, methyl iodide and acetic acid, and mixtures thereof. Make-up water may be introduced into the decanter 234 via stream 233.

At least a portion of the heavy, organic phase from the decanter 234 is sent via stream 238 to a distillation column, e.g., hydrocarbons removal column, alkanes column, etc. (depicted exemplary as 270 in FIGS. 2A and 2B) to separate MeI from hydrocarbon (e.g., heavy hydrocarbons, alkanes). In one example of an alkanes column or alkanes tower, the stream 238 is distilled to form a vapor stream having the majority of methyl iodide (over 50% of the methyl iodide from the heavy organic phase 238 from the decanter 234) and a bottoms stream having the majority of acetic acid, methyl acetate, methyl iodide, and the hydrocarbon impurities (over 50% of each component from the heavy organic phase 238 from the decanter 234).

The overhead temperature of the distillation in the alkanes column is generally below about 75° C. so that there is no significant amount of hydrocarbon impurities coming out with the vapor stream. In particular examples, the overhead temperature of the distillation is within the range of about 43° C. (boiling point of MeI) to about 75° C., about 43° C. to about 60° C., or about 43° C. to about 45° C. The closer the overhead temperature of the distillation to the boiling point of MeI, the less the amount of hydrocarbon impurities existing in the vapor stream. The vapor stream is recycled to the carbonylation reaction. Lowering the overhead temperature of the heavy phase distillation, although desirably reducing the hydrocarbon impurities in the vapor stream, results undesirably in a higher concentration of MeI in the bottoms stream. According to certain embodiments, the bottoms stream is disposed as a waste.

It should be noted that removal of the troublesome byproduct HAc from the acetic acid system 200 via physical or chemical techniques has occupied significant research time in the art over the last decade. This problematic byproduct and its aldehyde derivatives may unfortunately impact product purity. The HAc may also serve undesirably as a precursor to various hydrocarbons which impact decanter 234 heavy density, and as a precursor to higher alkyl iodides which may require expensive adsorption beds for their removal, for example.

As discussed below, the present techniques provide for an acid catalyzed and ion-exchange resin pathway which contains both kinetically-controlled and thermodynamically-controlled steps to convert HAc. As explained below, the initial kinetically-controlled oligomeric product, paraldehyde, has a favorably high boiling point in terms of removal by distillation but unfortunately decomposes when heated above 60° C. The thermodynamically-controlled product, crotonaldehyde (likely formed via an aldol condensation pathway), is stable to temperature and has a sufficiently high boiling point to be removed efficiently by distillation. Conditions, such as acid catalyst and resin concentration, can be tailored to facilitate rapid formation of the thermodynamically-controlled product. Acid catalyst or resin concentration and conditions can be tailored to facilitate the thermodynamically-favored crotonaldehyde to be formed rapidly and quantitatively. Crotonaldehyde, though thermally stable, may undergo a further reaction on supported catalysts to form one or more species.

Conversion of HAc

According to the present techniques, HAc may be removed from the acetic acid system 200 by providing a stream having HAc from the acetic acid system 200 and contacting the stream (e.g., 238) with an ion-exchange resin. As discussed in an alternate embodiment below, the stream (e.g., 238) having HAc may also be treated with liquid catalyst in addition to or in lieu of with ion-exchange resin. Upon contacting the stream with the ion-exchange resin or liquid catalyst, at least a portion of the HAc in the stream may be converted to an oligomer product, including paraldehyde and crotonaldehyde, for example.

At the outset, it should be noted that while the present disclosure focuses as an example on the treatment of stream 238 (decanter 234 heavy organic phase), other streams (having HAc) in the acetic acid system 200 may be treated ion-exchange resin (and/or with liquid catalyst) in accordance with the present techniques. For example, the stream 238 may be removed from the decanter 234 and at least a portion transferred to a distillation column (e.g., drying column 240, heavy-ends column 250, or combinations thereof), where an overhead stream having the solution (e.g., stream 242, stream 252, or combinations thereof) distilled from the heavy phase stream. That overhead stream may be contacted with the ion-exchange resin or liquid catalyst according to the disclosed process, for instance.

As indicated, the byproduct HAc in the acetic acid process 200 may be difficult to remove from the process. There are few places in the system where HAc is sufficiently concentrated to efficiently target its removal. One location where HAc is sufficiently concentrated is the decanter 234 and in particular, the decanter 234 heavy organic phase (stream 238) where HAc is concentrated to about 0.5 wt %, for example. Physical removal of HAc from this heavy phase via distillation may be difficult as the HAc boiling point (20.2° C.) is close to the principal component in the heavy organic phase, MeI (boiling point=42.5° C.). Thus, the present techniques take advantage of HAc's reactivity to convert HAc into high boiling (i.e., 100° C. or higher) derivatives that are more easily separated from the low boiling MeI by distillation.

Figure 2A:
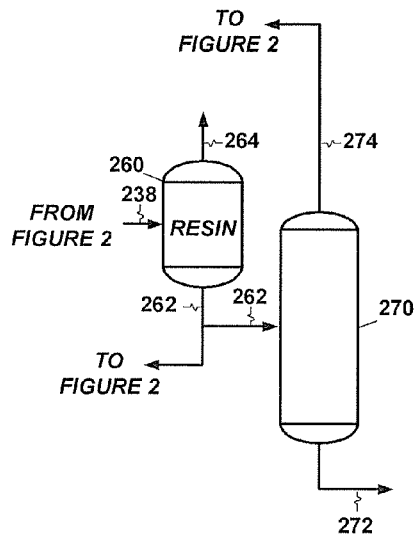
FIG. 2A is a schematic of an exemplary continuation of FIG. 2 in accordance with embodiments of the present techniques.

Referring to FIG. 2A, and according to the present techniques, at least a portion of the heavy organic phase (stream 238) is contacted with an ion-exchange resin, e.g., in a resin vessel 260, prior to introduction into the alkanes column 270 (mentioned above). In an embodiment, about 5% to about 100% by weight of the heavy, organic phase exiting the decanter 234 (i.e., in stream 238) is contacted with an ion-exchange resin. In other embodiments, about 5% to about 50% by weight of the heavy-organic phase exiting the decanter 234 is contacted with an ion-exchange resin. Portions of the remainder of the heavy-organic phase 238 exiting the decanter 234 may be recycled (see FIG. 2) to the reaction zone 202 and/or bypass (not shown) the resin vessel 260 (FIG. 2A) to the alkanes column 270, for example.

In resin vessel 260, HAc undergoes rapid acid catalyzed oligomerization to form paraldehyde in an equilibrium reaction which goes to about 75% completion, for example, depending on operating conditions in the resin vessel 260. Paraldehyde has a boiling point of 124° C. and thus would be a good candidate for separation from MeI by distillation. However, paraldehyde decomposes (back to HAc) upon heating to about 60° C., for instance, and thus while paraldehyde may be the kinetically-favored product of acid catalysis, it is not very stable. Therefore, paraldehyde may not be a suitable candidate in a downstream distillation for separation from MeI.

However, if the initial and rapidly formed paraldehyde is left in contact with the acid catalyst, the paraldehyde generally converts to the thermodynamically-favored crotonaldehyde. This is likely not a direct paraldehyde to crotonaldehyde conversion but rather occurs via paraldehyde reversion to HAc followed by aldol condensation in which two molecules of HAc react together to form crotonaldehyde. Crotonaldehyde has a boiling point of 102° C. and thus is another candidate to separate from the low boiling methyl iodide. Unlike paraldehyde, however, crotonaldehyde does not generally decompose to lower boiling compounds upon heating over modest temperatures and times.

Figure 2B:
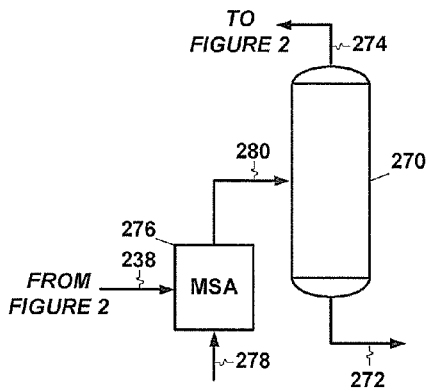
FIG. 2B is a schematic of an alternate exemplary continuation of FIG. 2 in accordance with embodiments of the present techniques.

In an alternate embodiment, FIG. 2B depicts a methanesulfonic acid (MSA) catalyst treatment system 276 in lieu of (or in addition to) employing a resin vessel 260 to treat stream 238. As understood by the skilled artisan, MSA may be employed as an unsupported liquid catalyst, for example. Again, stream 238 to be treated may include all of the decanter 234 heavy, organic phase or be a slipstream 238 of the decanter 234 heavy, organic phase, with any remainder of the heavy, organic phase recycled to the reaction zone 202 and/or sent directly to the alkanes column 270, for example. In the illustrated alternate embodiment of FIG. 2B, slipstream 238 is treated with MSA catalyst to convert the acetaldehyde in slipstream 238 to an oligomer such as crotonaldehyde. Unfortunately, the use of the MSA catalyst to treat slipstream may promote undesired side reactions and be equipment-intensive in implementation. Yet, as discussed below, the MSA catalyst, as with the ion-exchange resin, beneficially promotes the thermodynamically-favored crotonaldehyde over the kinetically-favored paraldehyde in the conversion of HAc.

FIG. 2B depicts the stream (or slipstream) 238 entering the MSA system 276 where liquid MSA catalyst 278 is mixed with stream 238 to convert the HAc in the stream 238 to an oligomer, such as crotonaldehyde. A stream 280 exiting the MSA system may resemble the composition of the entering stream 238, except that the HAc is substantially converted to crotonaldehyde, for example. In the illustrated example, stream 280 is sent to the alkanes column 270 where the crotonaldehyde is removed in the bottoms stream 272. The overhead stream having primarily methyl iodide may be recycled to the reaction area 202, such as to the flash vessel 220 (see FIG. 2).

In one example, the mixture of stream 238 and MSA 278 is flashed (i.e., depressured and/or heated) in the MSA system 276 after sufficient contact time to produce stream 280 (vapor) from the flashed mixture. The boiling point of MSA is generally significantly higher than the components in stream 238 and the yielded crotonaldehyde, such that the flash operation may not incorporate the liquid MSA in stream 280.

Moreover, as appreciated by one of ordinary skill in the art, unit operations other than a flash operation may be employed in the MSA system 278. For example, where phase separation may be defined, a decanter-type operation may be employed to recover the liquid MSA catalyst and forward a resulting stream 280 with the crotonaldehyde to the alkanes column 270. In another example, a stripper or counter-current flow device may be used to contact the liquid MSA catalyst with the entering stream 238 and to produce stream 280. Lastly, as indicated, streams other than stream 238 in the acetic acid system 200 having HAc may be processed in a MSA catalyst system.

Returning to FIG. 2A, in embodiments, contacting the solution with the ion-exchange resin (e.g., in resin vessel 260) may occur at room temperature, ambient temperature, or a temperature below the boiling point of HAc, and so on. In an embodiment, contacting the solution with the ion-exchange resin may occur for at least about 30 minutes. The mass ratio of aldehyde to ion-exchange resin may be in a range of about 0.1 to about 2.0, for example.

Thus, in an embodiment, a stream 238 is discharged from the heavy organic phase of the decanter 234. This heavy organic phase includes a solution of HAc and methyl iodide. At least a portion of the heavy organic phase (stream 238) may pass to the resin vessel 260, where the solution may be contacted with the ion-exchange resin according to the disclosed process. Moreover, it should be noted again that while certain embodiments focus on the decanter 234 heavy organic phase (stream 238) where acetaldehyde is present at about 0.5 wt %, for example, other streams having HAc (and MeI) in the acetic acid system 200 may be treated in accordance with the present techniques.

The ion-exchange resins, such as those that may be employed in resin vessel 260, may include strongly acidic ion-exchange resins, for example, such as AMBERLYST™ 15Dry. This is a bead form, strongly acidic ion exchange resin developed particularly for heterogeneous acid catalysis of a wide variety of organic reaction. It is available from The Dow Chemical Company and may be purchased therefrom over the World Wide Web of the Internet at www.dow.com. Additional information regarding this product may be found at http://www.dow.com/products/product/amberlyst-15dry/. It is also available from its subsidiary Rohm and Haas LLC, which can be contacted at 100 Independence Mall West, Philadelphia, Pa., USA, 19106-2399; Tel: +1 (215) 592-2503; Fax: +1 (215) 592-4534, along with additional information at www.amberlyst.com.

AMBERLYST™ 15Dry may be manufactured as opaque beads and may have a macroreticular pore structure with hydrogen ion sites located throughout each bead. The surface area may be about 53 $m^2/g$, the average pore diameter may be about 300 Angstroms, and the total pore volume may be about 0.40 cc/g. AMBERLYST™ 15Dry may be utilized in essentially non-aqueous systems (e.g., less than 1 wt % water). Therefore, the solution may be essentially or substantially nonaqueous with use of AMBERLYST™ 15Dry.

HAc by virtue of its polar carbonyl group is very reactive. Oligomerization in a MeI/HAc solution to paraldehyde may only slowly take place without any acid catalyst being present. In contrast, in the presence of a small amount of acid catalyst resin such as Amberlyst 15, this oligomerization of HAc to paraldehyde is essentially instantaneous, as constructed in FIG. 3 (and with liquid unsupported catalyst MSA in FIG. 5). Notably, generally regardless of the nature of the acid resin catalyst or the catalyst concentration, oligomerization only goes to about 75% completion in certain embodiments, indicating an equilibrium reaction.

Figure 3:
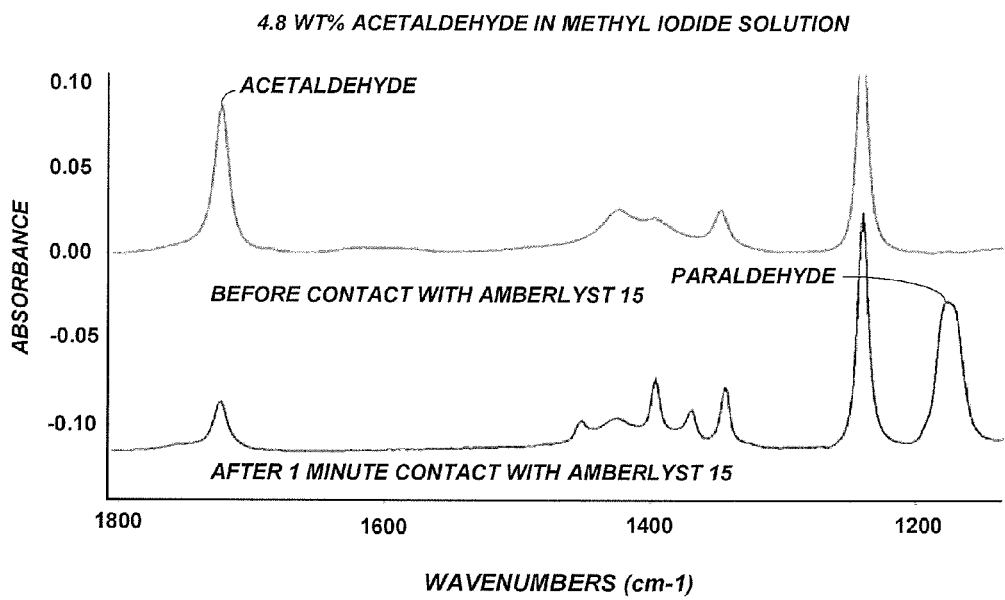
FIG. 3 is an overlaid graph of in-situ infrared spectra for a solution of acetaldehyde ("HAc") and methyl iodide ("MeI") contacted with an ion-exchange resin in accordance with embodiments of the present techniques.

FIG. 3 shows overlaid in-situ infrared spectra for a solution of 4.8 wt % HAc and MeI contacted with an ion-exchange resin (AMBERLYST™ 15Dry), taken with an infrared spectrometer. In the illustrated embodiment of FIG. 3, the mass ratio of HAc to ion-exchange resin is 1:2. Spectra are shown for time values of zero minutes and 1 minute. While that paraledyde appearance in the solution is rapid, there is a very small amount of contact time experienced for the initial paraldehyde presence that rapidly arises. For clarity, it should be noted that the zero minutes in FIG. 3 is defined after this very small amount of time and at the beginning of the paraldehyde decay.

Figure 4:
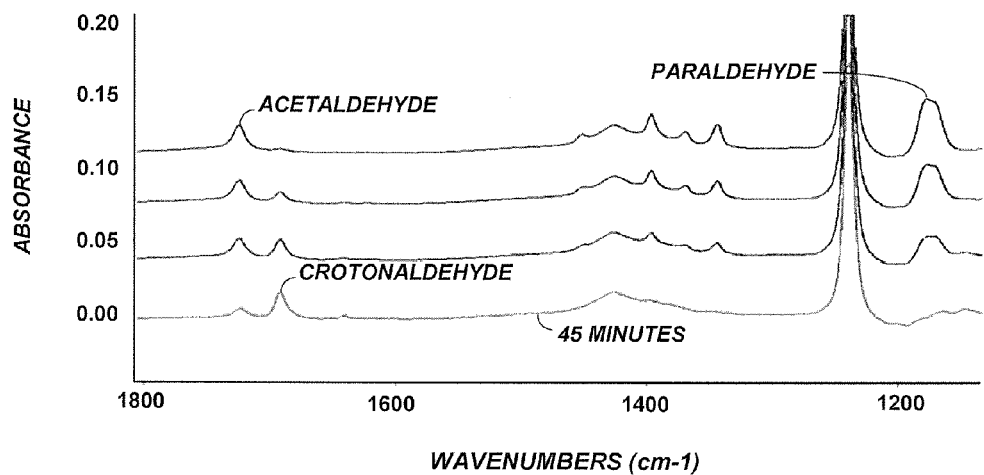
FIG. 4 is an overlaid graph of in-situ infrared spectra for a solution of HAc and MeI contacted with an ion-exchange resin in accordance with embodiments of the present techniques.

The HAc undergoes aldol condensation to form crotonaldehyde, as indicated in FIG. 4. Indeed, the infrared spectra in FIG. 4 shows the acid catalyzed conversion of initially formed paraldehyde to crotonaldehyde over a 45 minute period at room temperature with the initial solution of HAc and MeI contacted with the ion-exchange resin. The overlaid infrared spectra in FIG. 4 (the same solution and time continuation of FIG. 3) shows that with the initial, rapid acid resin catalyzed conversion of HAc to paraldehyde at room temperature, when the solution is monitored over time, the initial, rapidly formed paraldehyde essentially disappears with simultaneous formation of the aldol condensation produced, crotonaldehyde. Overlaid spectra showing this behavior are contained in FIG. 4. In particular, FIG. 4 shows an overlaid in-situ infrared spectra for a solution of HAc and MeI contacted with an ion-exchange resin (AMBERLYST™ 15Dry), taken with an infrared spectrometer.

It is believed that separate kinetically and thermodynamically controlled steps are being observed as there is no apparent direct route from paraldehyde to crotonaldehyde. In other words, slower aldol condensation of acetaldehyde to crotonaldehyde, leads to a shift in the acetaldehyde/paraldehyde equilibrium towards the thermodynamically-favored crotonaldehyde product. Similar behavior was observed in decanter 234 organic, heavy-phase type solutions containing HOAc, MeOAc and alkanes in addition to MeI and HAc.

In order to investigate this effect in unsupported acids, several unsupported acid catalysts were examined. In contrast to Amberlyst 15 where oligomerization is rapid at room temperature, oligomerization with unsupported acid catalysts in certain examples proceeds only very slowly in the presence of 85% phosphoric acid, for example, and generally no crotonaldehyde is observed. In addition, no general dependence on acid concentration is observed. The slow paraldehyde formation and absence of crotonaldehyde are believed due to the aqueous content of $H_3PO_4$. Water ($H_2O$) is a polymerization inhibitor for HAc and will also suppress the dehydration step of aldol condensation, for example.

Figure 5:
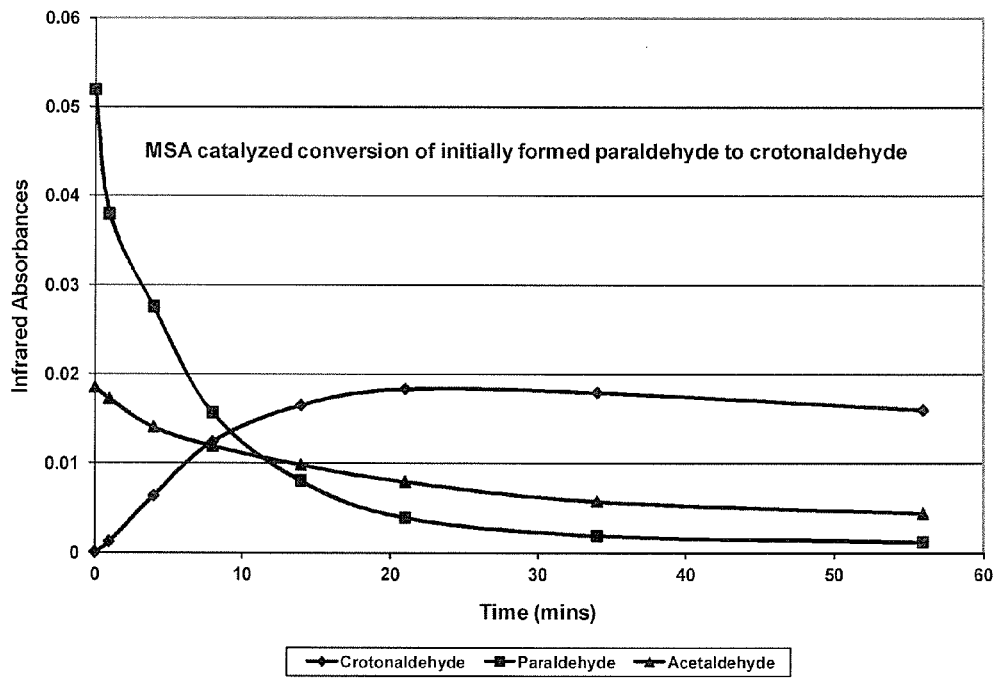
FIG. 5 is a graph of infrared absorbance versus time for a solution of HAc and MeI contacted with methanesulfonic acid (MSA) in accordance with embodiments of the present techniques.

In order to avoid this undesired aqueous component of mineral acids, the strong mineral methanesulfonic acid (MSA), for example, is employed. With MSA as an unsupported liquid acid catalyst, behavior similar to Amberlyst 15 was observed in that rapid paraldehyde formation was accompanied by slower crotonaldehyde formation, as shown in FIG. 5 which defines time zero as the beginning of rapidly-formed paraldehyde decay. Moreover, as observed with Amberlyst 15, the rate of crotonaldehyde formation (paraldehyde decay) is dependent on acid concentration (see FIG. 7).

FIG. 5 shows a graph of infrared absorbance versus time for a solution of HAc and MeI contacted with MSA. The graph includes infrared absorbance plots for crotonaldehyde, paraldehyde, and HAc. The mass ratio of HAc to MSA is 1:3. The components were contacted at room temperature. As can be seen with the infrared absorbance of paraldehyde, an initial large presence is realized followed by a sharp drop concluding with a gradual reduction to a negligible amount. The infrared absorbance of HAc gradually decreases, and the infrared absorbance of crotonaldehyde gradually increases to substantially leveling off with a slight decrease. Lastly, it should be noted that time zero on the plot in FIG. 5 refers to the point at which about 75% of staring HAc has already substantially instantly converted to paraldehyde.

Removal of Crotonaldehyde after Contact with Resin

As discussed as conventional, a slipstream 238 of the decanter 234 heavy phase may be passed to a distillation column 270 (e.g., called the alkanes tower) to remove byproduct hydrocarbons in a high-boiling bottoms stream 272. The overhead stream 274 (low boilers, primarily MeI and HAc) of the alkanes tower 270 is recycled to the process (e.g., to the reaction area 202) while the bottoms stream 272 (high boilers) is disposed of as waste in certain examples.

Referring to FIG. 2A, and as indicated with the present techniques, the disclosed process may deliberately promote formation of oligomer product (e.g., crotonaldehyde) in the acetic acid system 200, such as in the slipstream 238 sent to the alkanes column 270. For example, in certain embodiments, a portion or all of stream 238 may be sent through a slurry bed of ion-exchange resin (e.g., Amberlyst 15 resin in vessel 260) to convert HAc to crotonaldehyde. A portion of stream 238 may optionally bypass (not shown) the resin vessel 260 and be fed directly to the alkanes column 270.

The present techniques consider a variety of scenarios for removal of the formed crotonaldehyde. Two basic exemplary scenarios include a first scenario (or scenario 1) and a second scenario (or scenario 2). In the first scenario, the crotonaldehyde formed remains in solution and is passed on to the alkanes column 270 for removal via the bottoms waste stream 272. In a second basic scenario, the crotonaldehyde is fully adsorbed onto the resin in vessel 260, and later removed from the system 200 via regeneration of the resin in vessel 260. Moreover, various scenarios may exist between the first and second scenarios, where only some of the crotonaldehyde in adsorbed onto the resin in vessel 260, for instance.

As indicated in the aforementioned first scenario, the crotonaldehyde formed remains in solution in the resin vessel 260 and is passed on to the alkanes column 270 in the treated stream 238 labeled as stream 262. This treated stream 238, labeled as stream 262, discharges from the resin vessel 260 and is sent onwards to the alkanes tower 270 (FIG. 2A) where crotonaldehyde will be removed in the bottoms waste stream 272 along with the byproduct hydrocarbons (alkanes including heavy alkanes). Of course, bottoms stream 272 may be further processed instead of disposed as waste.

In the aforementioned second scenario, the crotonaldehyde formed (e.g., in resin vessel 260) is fully adsorbed onto the ion-exchange resin (e.g., in resin vessel 260). Thus, the treated stream 238, labeled at stream 262, is substantially free of HAc (converted to crotonaldehyde) and free of the formed crotonaldehyde (adsorbed onto the resin). The stream 262 may be sent to the alkanes column 270 and/or recycled to the reaction zone 202, for example. In general, while not depicted in FIGS. 2 and 2A, stream 262 in scenario 2 may also be recycled to the decanter 234, light-ends column 230, reactor 210, other point in system 200, or combinations thereof. The stream 262 generally includes MeI which is desirable to recover and reuse in the system 200.

In scenario 2 of adsorption of crotonaldehyde onto the resin, the resin once saturated or prior to saturation can be regenerated offline to recover via stream 264 the crotonaldehyde adsorbed on the resin. Of course, depending on the operating conditions of the regeneration, the crotonaldehyde desorbed from the resin may discharge in stream 264 as different species. Moreover, again, as for the treated stream 262 discharged from the resin vessel 260 when not in regeneration, this heavy phase 262 is depleted in both HAc and crotonaldehyde in scenario 2, and can be recycled directly to the process (e.g., to the reactor 210 via stream 212, as shown in FIG. 2), and/or sent to alkanes tower 270 for removal of byproduct hydrocarbons, as shown in FIG. 2A.

Again, with regard to the second scenario, the crotonaldehyde formed in the presence of Amberlyst 15 acid resin may be substantially fully adsorbed. However, less than full adsorption onto the resin may be realized, depending on the resin concentration, temperature and contact time with resin, and so on. For example, FIGS. 6 and 7 indicate the degree of adsorption of the crotonaldehyde on the resin as a function of temperature and resin concentration, respectively.

Figure 6:
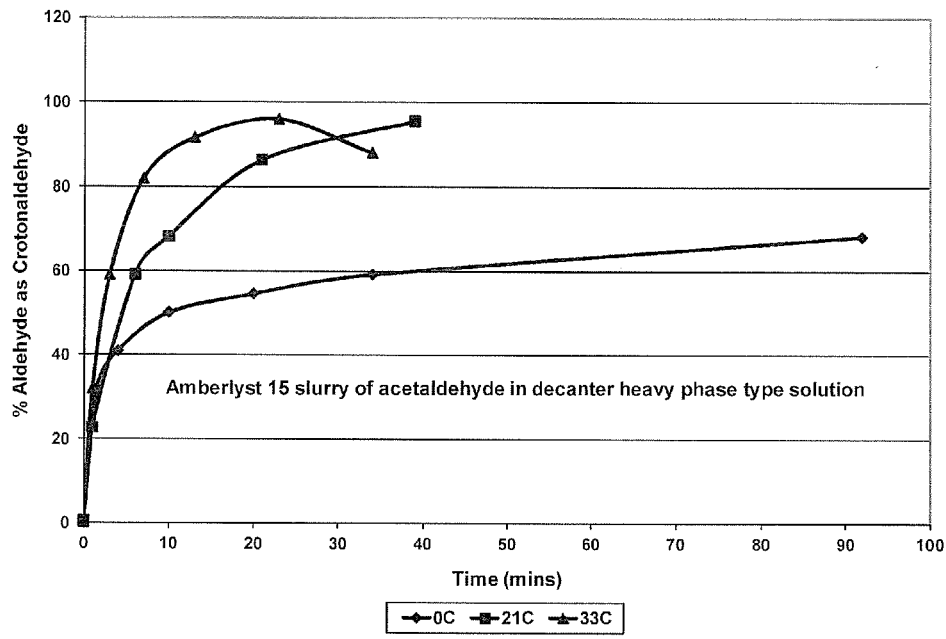
FIG. 6 is a graph of % HAc as crotonaldehyde versus time for a solution of MeI and HAc contacted with ion-exchange resin at three different temperatures in accordance with embodiments of the present techniques.

FIG. 6 is a graph of % HAc as crotonaldehyde versus time for a solution of MeI and HAc contacted with ion-exchange resin at three different temperatures. Three plots at different temperatures are depicted. The plot at 0° C. and the plot at 21° C. both show the presence of crotonaldehyde (from the HAc) in solution as increasing. In contrast, the plot at 33° C. shows the crotonaldehyde (from HAc) in solution increasing initially but beginning to decrease at about 25 minutes, indicating that crotonaldehyde is leaving the solution and being adsorbed onto the resin. In all, it is established in FIG. 6 that the rate of crotonaldehyde formation increases with temperature suggesting that commercially feasible rates could be accessed at temperatures beyond constraints of laboratory equipment employed. Further, as mentioned and indicated in FIG. 6, in the run carried out at 33° C., the formed crotonaldehyde may start eventually disappearing from solution, i.e., adsorbed onto the resin.

Figure 7:
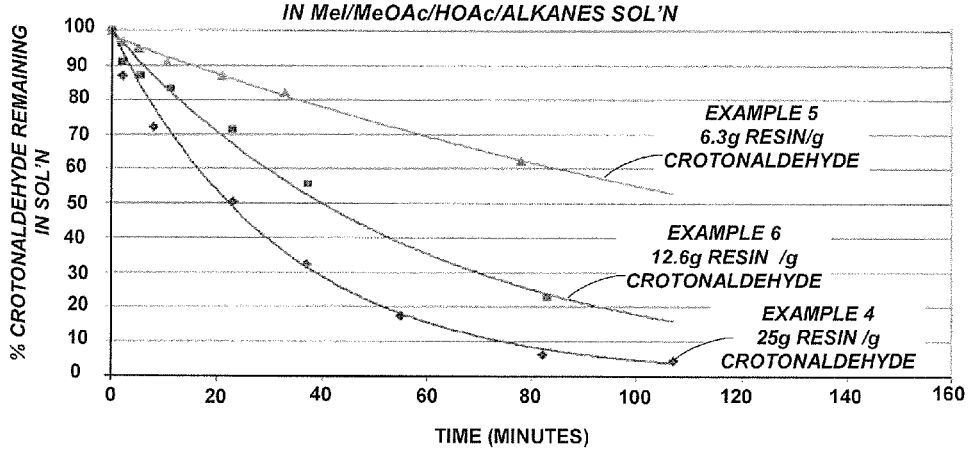
FIG. 7 is a graph of % crotonaldehyde remaining in solution versus time for heavy-phase type solution contacted with an ion-exchange resin at three different resin concentrations in accordance with embodiments of the present techniques.

In order to confirm and investigate this effect, a heavy phase type solution i.e., containing HOAc, MeOAc and alkanes in addition to MeI) was prepared which contained commercial crotonaldehyde but no HAc. Amberlyst 15 slurries containing varying resin loadings were then heated in sealed vials at 33° C. and monitored periodically. FIG. 7 depicts results and is a graph of % crotonaldehyde remaining in solution versus time for a solution of HAc and MeI contacted with an ion-exchange resin at three different resin concentrations. In particular, three plots at different Amberlyst 15 resin concentration corresponding respectively to Examples 4-6 below are depicted.

FIG. 7 shows that the % crotonaldehyde remaining in solution is less at greater time and less at greater resin concentrations, thus indicating that more crotonaldehyde is adsorbed onto the resin (as opposed to remaining in solution) over time and at greater resin concentration (i.e., greater amounts of resin). Indeed, as shown in FIG. 7, crotonaldehyde disappears with the rate of disappearance directly dependent on acid concentration. No other new infrared peak was observed, suggesting that crotonaldehyde is either adsorbing directly on the resin or is decomposing to some other species that is adsorbing on the resin.

Thus, the nature of the products and product distribution may be functions of several variables such as resin concentration, resin contact time and temperature, and so on. With this is mind, an operating temperature, for example, of resin vessel 260 may be specified to drive that the crotonaldehyde remain in solution, or conversely, that the crotonaldehyde adsorb onto the resin.

If it is desired that the crotonaldehyde formed in resin slurry or on a resin flow-through bed remain unadsorbed and pass out in the eluate, then an exemplary temperature range of 0 to 30° C. may be specified, for example. On the other hand, if it is desired that the crotonaldehyde formed in resin slurry or on a resin flow-through bed be adsorbed, then temperatures in excess of 30° C. may be specified, for example. The upper temperature being limited by pressure ratings of vessels used to contain the resin slurry or bed, for instance.

It will be understood by those skilled in the art and from the examples provided that a wide range of conditions exist in terms of manipulation of temperature and acid catalyst concentration, where 100% crotonaldehyde adsorption, 0% crotonaldehyde adsorption, or partial crotonaldehyde adsorption can be achieved. Individual producers can choose to allow crotonaldehyde adsorption and periodically regenerate the resin or to allow crotonaldehyde to elute off the resin and dispose of the eluate as waste (via stream 264), for example.

In cases of partial adsorption or full adsorption (scenario 2), the ion-exchange resin may be regenerated to remove the components adsorbed onto the resin. To regenerate the ion-exchange resin, the resin may be heated and the adsorbed components (e.g., crotonaldehyde) desorbed and discharged from the resin vessel 260 via stream 264. Stream 264 may be recovered or disposed as waste.

In one or more embodiments, the disclosed process may be performed in a continuous format. For example, two resin beds or two resin vessels (e.g., two resin vessels 260) may be disposed in parallel, and while one is being regenerated, the other is in operation. On the other hand, the disclosed process may be performed in a batch format. The resin vessel 260 may be in continuous or batch operation and may include a tank of dimension and material as known in the industry for production of acetic acid.

In all with regard to the ion-exchange resin, after converting HAc to oligomer product (e.g., crotonaldehyde), the oligomer product may be removed from the solution, for example, by adsorbing at least a portion of the oligomer product onto the ion-exchange resin to yield an adsorbent resin product, and/or by forwarding the solution (stream 262) having the non-adsorbed oligomer product (to be removed) to further processing such as to alkanes column 270 where the oligomer product is removed in the bottoms stream 272. In the cases with the crotonaldehyde adsorbed onto the resin, the solution should be partially or substantially depleted of HAc and crotonaldehyde, and the remaining MeI may be recovered from the solution, for example in sending stream 262 to the alkanes column 270 with MeI exiting in the overhead stream 274 of the alkanes column 270. The stream 262 may also be recycled to in the system 200, especially if substantially depleted of HAc and crotonaldehyde. In the cases where the crotonaldehyde is not adsorbed or only partially adsorbed on the resin, the stream 262 may be sent to the alkanes column 270, the MeI recovered in the overhead stream 274 and the crotonaldehyde discharged in the bottoms stream 272 (e.g., as waste).

The adsorbent product (i.e., resin having adsorbed oligomer) in resin vessel 260 may then be separated into (1) oligomer or HAc and (2) a regenerated ion-exchange resin. In an embodiment, the adsorbent product may be heated to a temperature above about 21° C. in order to separate oligomer and/or HAc from the resin to regenerate the ion-exchange resin (e.g., by desorption of oligomer and/or HAc gas in resin vessel 260). Desorbed oligomer and/or desorbed HAc may be recovered in stream 264. In a specific embodiment, the adsorbent product (resin) may be heated to a temperature of about 80° C. or more in order to separate HAc to regenerate the ion-exchange resin.

SUMMARY

The present techniques may involve a method for removing acetaldehyde from an acetic acid system, including providing a solution having at least methyl iodide and acetaldehyde from the acetic acid system, and contacting the solution with an ion-exchange resin (e.g., a strongly acidic ion-exchange resin) to convert at least a portion of the acetaldehyde to yield an oligomer including crotonaldehyde and which may be removed from the solution. Removing the oligomer or crotonaldehyde may include distilling the solution and discharging the oligomer in a bottom stream, and/or adsorbing at least a portion of the oligomer onto the ion-exchange resin, and further regenerating the ion-exchange resin to remove the oligomer from the acetic acid system. The method may also include recovering methyl iodide from the solution, and recycling the recovered methyl iodide to within the acetic acid system. In certain embodiments, the solution is contacted with the ion-exchange resin at room temperature for at least about 30 minutes, and wherein the mass ratio of HAc to ion-exchange resin is in a range of about 0.5 to about 2.0. The method may account for the acetic acid system having a decanter, the method including removing a heavy phase stream having the solution from the decanter, and passing the heavy phase stream to a resin vessel having the ion-exchange resin, and wherein contacting the solution is performed in the resin vessel. Regenerating the resin may include heating the ion-exchange resin to a temperature above about 21° C., for example, and separating the oligomer from the ion-exchange resin. On the other hand, regenerating may include heating the ion-exchange resin having the adsorbed oligomer to a temperature of about 80° C. or greater, and separating the oligomer from the ion-exchange resin.

The present techniques may also provide for a method of operating an acetic acid production system, including flashing a reaction mixture discharged from an acetic acid production reactor into a vapor stream and a liquid stream, the vapor stream comprising acetic acid, water, methanol, methyl acetate, methyl iodide, and acetaldehyde. The method includes distilling the vapor stream into: (1) a product side stream comprising acetic acid and water; (2) a bottoms stream; and (3) an overhead stream comprising methyl iodide, water, methyl acetate, acetic acid, and acetaldehyde. This method further includes condensing the overhead stream into: (1) a light, aqueous phase comprising water, acetic acid, and methyl acetate; and (2) a heavy, organic phase comprising methyl iodide, acetic acid, water, and the acetaldehyde. The method includes converting the acetaldehyde in at least a portion of the heavy, organic phase to an oligomer. Such a conversion may occur by contacting the at least a portion of the heavy, organic phase with an ion-exchange resin and/or with a liquid MSA catalyst. This method of operating an acetic acid production system may include may include adsorbing the oligomer (e.g., crotonaldehyde) onto the ion-exchange resin, and regenerating the ion-exchange resin to separate the crotonaldehyde from the ion-exchange resin. The method may include distilling the at least a portion of the heavy, organic phase after contact with the ion-exchange resin into a vapor stream having methyl iodide and a bottoms stream having the oligomer (e.g., crotonaldehyde).

The present techniques provide for a method of producing acetic acid, including reacting methanol and carbon monoxide in the presence of a carbonylation catalyst to produce a crude stream having the produced acetic acid. This method includes purifying the crude stream to produce a product stream having the acetic acid, wherein the purifying generates a methyl iodide stream having at least methyl iodide acetaldehyde. The method involves contacting the methyl iodide stream with an ion-exchange resin to convert the acetaldehyde to crotonaldehyde to reduce an amount of acetaldehyde in the production of acetic acid.

Lastly, the present techniques provide for an acetic acid production system including: a reactor to react methanol and carbon monoxide in the presence of a carbonylation catalyst to form acetic acid; a flash vessel that receives a reaction mixture comprising the acetic acid from the reactor; a distillation column that receives a vapor stream from the flash vessel; a decanter that receives a condensed overhead stream from the distillation column; and a resin vessel that receives a heavy, organic phase having at least methyl iodide and acetaldehyde from the decanter, the resin vessel having an ion-exchange resin to convert the acetaldehyde to an oligomer. In this example, a majority by weight of the heavy, organic phase is methyl iodide, and the oligomer includes crotonaldehyde.

EXAMPLES

The following investigations and examples are intended to be illustrative only, and are not intended to be, nor should they be construed as, limiting the scope of the present invention in any way.

In Examples 1-7, infrared spectra were collected on a Nicolet 6700 FUR spectrometer obtained from Thermo Scientific. The spectrometer was equipped with a Smart Miracle accessory also obtained from Thermo Scientific. The accessory contained a 3 bounce, zinc selenide ATR crystal. Those skilled in the art of infrared spectroscopy will realize that use of such an accessory will allow infrared absorbance peaks of HAc, crotonaldehyde and paraldehyde to be monitored and quantified. Examples 1-7 address static slurries or mixtures. Examples 8 and 9 address a flow-through bed mode.

Figure 8:
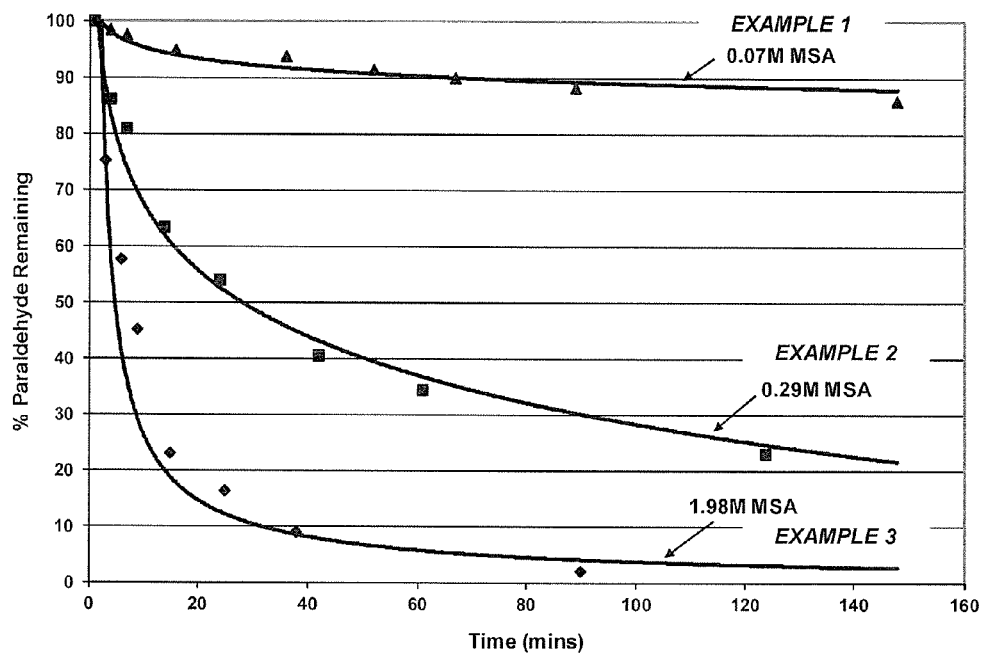
FIG. 8 is a graph of % paraldehyde remaining versus time for a solution of HAc and MeI contacted with MSA at three different amounts of MSA in accordance with embodiments of the present techniques.
Figure 9:
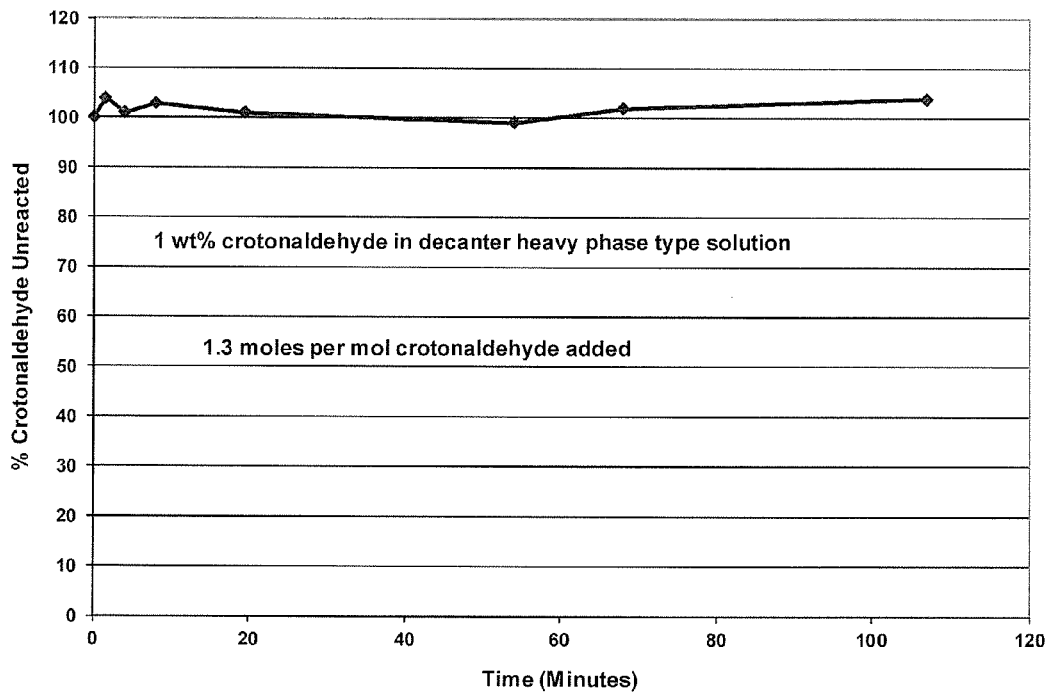
FIG. 9 which is a graph of % crotonaldehyde unreacted in solution versus time.

Examples 1-3 are associated with FIG. 8 which is a graph of % paraldehyde remaining versus time. Three plots at different MSA concentrations are given corresponding respectively to Examples 1-3. Examples 4-6 are associated with FIG. 7 mentioned above, which is a graph of % crotonaldehyde remaining in solution versus time. Three plots at different Amberlyst 15 resin concentrations corresponding respectively to Examples 4-6 are depicted. Example 7 is associated with FIG. 9 which is a graph of % crotonaldehyde unreacted versus time. A single plot depicts am essentially flat curve at 100% crotonaldehyde unreacted over time.

Example 1

An amount of 0.013 grams of methanesulfonic acid (MSA) was added via syringe to 4 grams of a solution composed of 4 wt % acetaldehyde and 96 wt % methyl iodide in a septum sealed 5 mL vial at room temperature. Aliquots of solution were periodically removed by syringe and infrared spectra obtained. The conversion of the rapidly formed paraldehyde to crotonaldehyde could be monitored by measuring either the decrease in absorbance of a paraldehyde peak at 1172 wavenumbers or the increase in absorbance of a crotonaldehyde peak at 1695 wavenumbers. After 2 hours, about 14% conversion of paraldehyde to crotonaldehyde had taken place.

Example 2

Example 1 was repeated with the exception that 0.054 grams of MSA was used. After 2 hours, about 75% conversion of paraldehyde to crotonaldehyde had taken place.

Example 3

Example 1 was repeated with the exception that 0.37 grams of MSA was used. After 90 minutes, about 95% conversion of paraldehyde to crotonaldehyde had taken place.

Example 4

4.0 grams of a solution composed of 1.0 wt % crotonaldehyde, 3.5 wt % acetic acid, 9.3 wt % methyl acetate, 10.0 wt % 2,3-dimethylpentane and 76.2 wt % methyl iodide was heated to 33 C in a septum sealed 5 mL vial. This solution was syringed into another septum sealed vial containing 0.25 grams of Amberlyst 15, also maintained at 33° C. Solution crotonaldehyde concentration was periodically monitored by removing aliquots of solution via syringe, obtaining an infrared spectrum and measuring the absorbance of a crotonaldehyde peak at 1695 wavenumbers. After 80 minutes, about 40% of the crotonaldehyde had been adsorbed on the resin.

Example 5

Example 4 was repeated with the exception that 0.50 grams of Amberlyst 15 was used. After 80 minutes, about 75% of the crotonaldehyde had been adsorbed on the resin.

Example 6

Example 4 was repeated with the exception that 1.0 grams of Amberlyst 15 was used. After 80 minutes, about 90% of the crotonaldehyde had been adsorbed on the resin.

Example 7

Example 4 was repeated with the exception that methanesulfonic acid was used as the acid catalyst, 0.07 grams of methanesulfonic acid, heated to 33 C, was added to 4.0 grams of the solution as described in Example 1. At 110 minutes, 0% of the crotonaldehyde had disappeared from solution.

Example 8

A solution composed of 9.5 wt % HAc dissolved in methyl iodide was passed in continuous downward flow mode at room temperature through a 10 gram bed of Amberlyst 15 maintained between layers of glass wool in a glass column with a length to diameter ratio of 1.6. An approximate flow rate of 4 bed volumes per hour (BV/hr) was maintained for 35 minutes. In order to reduce volatilization, feedstock was passed through a water condenser placed at the top of the column. Similarly, in order to reduce volatilization of eluted aliquots, such aliquots were collected into vials contained within an ice bath.

Infrared analysis of aliquots collected every 3 minutes showed a steady state concentration of 1.9 wt % acetaldehyde in the eluate, indicating an 80% conversion. Of the 7.6 wt % acetaldehyde that had reacted on the column, infrared analysis showed that 75% was present in the eluate as crotonaldehyde and 15% was present as paraldehyde. The unaccounted 10% is a combination of accuracy limits of infrared quantitation and of adsorption of small amounts of crotonaldehyde on the bed.

Example 9

A solution of 1.8 wt % acetaldehyde in a decanter heavy phase type solution composed of 77.7 wt % methyl iodide, 9.3 wt % methyl acetate, 4.7 wt % acetic acid, 3.5 wt % dodecane, and 3.0 wt % 2-methylpentane was passed through an Amberlyst 15 bed as described in Example 1. A flow rate of about 8 BV/hr was maintained for 1.7 hours. Infrared analysis of aliquots showed 77% conversion of acetaldehyde. Of the 1.4 wt % acetaldehyde that had reacted on the column, infrared analysis showed that 60% was present in the eluate as crotonaldehyde and 40% was present as paraldehyde.

INCORPORATED REFERENCES

The following patents are hereby incorporated by reference in their entirety and for all purposes as if expressly set forth verbatim herein:

U.S. Pat. No. 6,552,221, entitled, "Process control for acetic acid manufacture", and issued Apr. 22, 2003, to Milienium Petrochemicals, Inc., as assignee of the inventors Hallinan et al.

U.S. Pat. No. 5,817,869, entitled, "Use of Pentavalent Group VA Oxides in Acetic Acid Processing", and issued Oct. 6, 1998, to Quantum Chemical Corporation, as assignee of the inventors Hinnenkamp et al.

U.S. Pat. No. 5,932,764, entitled, "Iridium-Catalyzed Carbonylation Process for the Production of a Carboxylic Acid", and issued Aug. 3, 1999, to BP Chemicals Limited, as assignee of the inventors Morris et al.

U.S. Pat. No. 8,076,512, entitled, "Preparation of Acetic Acid", and issued Dec. 13, 2011, to Equistar Chemicals L.P. and Lyondell Chemical Technology, as assignees of the inventors Fitzpatrick et al.

U.S. Pat. No. 7,524,988, entitled, "Preparation of Acetic Acid", and issued Apr. 28, 2009, to BP Chemicals Limited, Equistar Chemicals L.P. and Lyondell Chemical Technology, as assignees of the inventors Harris et al.

In the event of conflict between one or more of the incorporated patents and the present disclosure, the present specification, including definitions, controls.

DESCRIPTION CLOSING

This concludes the detailed description. The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

We claim:

1. A method for removing acetaldehyde from an acetic acid system, comprising:
    providing a solution comprising methyl iodide and acetaldehyde from the acetic acid system; and
    contacting the solution with an ion-exchange resin, wherein contacting the solution with the ion-exchange resin converts at least a portion of the acetaldehyde to yield an oligomer
    wherein the oligomer comprises crotonaldehyde.

2. The method of claim 1, comprising removing the oligomer from the solution.

3. The method of claim 2, wherein removing comprises distilling the solution and discharging the oligomer in a bottom stream of the distilling.

4. The method of claim 2, wherein removing comprises adsorbing at least a portion of the oligomer onto the ion-exchange resin, and further comprising regenerating the ion-exchange resin.

5. The method of claim 4, wherein regenerating comprises:
heating the ion-exchange resin to a temperature above about 21° C.; and
separating the oligomer from the ion-exchange resin.

6. The method of claim 4, wherein regenerating comprises heating the ion-exchange resin having the adsorbed oligomer to a temperature of about 80° C. or greater.

7. The method of claim 1, comprising recovering methyl iodide from the solution, and recycling the recovered methyl iodide to within the acetic acid system.

8. The method of claim 1, wherein the solution comprises less than 1 wt % water, and wherein the ion-exchange resin comprises a strongly acidic ion-exchange resin.

9. The method of claim 1, wherein contacting the solution with the ion-exchange resin occurs at room temperature for at least about 30 minutes, and wherein the mass ratio of aldehyde to ion-exchange resin is in a range of about 0.1 to about 2.0.

10. The method of claim 1, wherein the acetic acid system comprises a decanter, the process further comprising removing a heavy phase stream comprising the solution from the decanter, and passing the heavy phase stream to a resin vessel comprising the ion-exchange resin, and wherein contacting the solution is performed in the resin vessel.

11. A method of operating an acetic acid production system, comprising:
(i) flashing a reaction mixture discharged from an acetic acid production reactor into a vapor stream and a liquid stream, the vapor stream comprising acetic acid, water, methanol, methyl acetate, methyl iodide, and acetaldehyde;
(ii) distilling the vapor stream into: (1) a product side stream comprising acetic acid and water; (2) a bottoms stream; and (3) an overhead stream comprising methyl iodide, water, methyl acetate, acetic acid, and acetaldehyde;
(iii) condensing the overhead stream into: (1) a light, aqueous phase comprising water, acetic acid, and methyl acetate; and (2) a heavy, organic phase comprising methyl iodide, acetic acid, water, and the acetaldehyde;
(iv) converting the acetaldehyde in at least a portion of the heavy, organic phase to an oligomer, wherein the converting step comprises contacting the at least a portion of the heavy, organic phase with an ion-exchange resin to convert the acetaldehyde to the oligomer; and
(v) distilling the at least a portion of the heavy, organic phase after contact with the ion-exchange resin into a vapor stream comprising methyl iodide and a bottoms stream comprising the oligomer, wherein the oligomer is crotonaldehyde.

12. The method of claim 11, comprising:
adsorbing the oligomer onto the ion-exchange resin, wherein the oligomer comprises crotonaldehyde; and
regenerating the ion-exchange resin to separate the crotonaldehyde from the ion-exchange resin.

13. The method of claim 11, wherein converting comprising contacting the at least a portion of the heavy, organic phase with methanesulfonic acid (MSA) as a catalyst to convert the acetaldehyde to the oligomer.

14. A method of producing acetic acid, comprising:
reacting methanol and carbon monoxide in the presence of a carbonylation catalyst to produce a crude stream comprising acetic acid;
purifying the crude stream to produce a product stream comprising the acetic acid, wherein the purifying generates a methyl iodide stream comprising methyl iodide acetaldehyde; and
contacting the methyl iodide stream with an ion-exchange resin to convert the acetaldehyde to crotonaldehyde to reduce an amount of acetaldehyde in an acetic acid system producing the acetic acid.

15. An acetic acid production system comprising:
a reactor to react methanol and carbon monoxide in the presence of a carbonylation catalyst to form acetic acid;
a flash vessel that receives a reaction mixture comprising the acetic acid from the reactor;
a distillation column that receives a vapor stream from the flash vessel;
a decanter that receives a condensed overhead stream from the distillation column; and
a resin vessel that receives a heavy, organic phase comprising methyl iodide and acetaldehyde from the decanter, the resin vessel having an ion-exchange resin to convert the acetaldehyde to an oligomer
wherein a majority by weight of the heavy, organic phase is methyl iodide, and
wherein the oligomer comprises crotonaldehyde.

* * * * *